United States Patent [19]

Morgan, Jr.

[11] Patent Number: 5,100,378
[45] Date of Patent: Mar. 31, 1992

[54] ENHANCEMENT OF TARGET CELL LOCALIZATION OF LYMPHOID CELLS

[75] Inventor: A. Charles Morgan, Jr., Edmonds, Wash.

[73] Assignee: NeoRx Corporation, Seattle, Wash.

[21] Appl. No.: 364,357

[22] Filed: Jun. 9, 1989

[51] Int. Cl.$^5$ ............................................. A61M 31/00
[52] U.S. Cl. ..................................... 604/49; 128/898; 424/9
[58] Field of Search ................... 424/1.1, 9; 604/48, 604/49, 50, 51, 52, 53; 128/898

[56] References Cited

U.S. PATENT DOCUMENTS

| | | | |
|---|---|---|---|
| 4,518,584 | 5/1985 | Mark et al. | 424/85.2 |
| 4,599,304 | 7/1986 | Lanier et al. | 435/7 |
| 4,692,405 | 9/1987 | Freedman | 435/7 |
| 4,753,927 | 6/1988 | Hahn | 514/13 |
| 4,764,359 | 8/1988 | Lemelson | 424/1.1 |
| 4,816,442 | 3/1989 | McPherson et al. | 514/12 |
| 4,816,449 | 3/1989 | Hahn | 514/17 |
| 4,861,589 | 7/1989 | Ju | 424/93 |
| 4,863,727 | 9/1989 | Zimmerman et al. | 424/85.2 |
| 4,935,223 | 6/1990 | Phillips | 424/1.1 |
| 4,963,354 | 10/1990 | Shepard et al. | 424/85.1 |
| 4,975,278 | 12/1990 | Senter et al. | 424/94.3 |
| 4,977,245 | 12/1990 | Jones | 530/531 |
| 4,980,160 | 12/1990 | Goldenberg et al. | 424/85.1 |
| 4,986,979 | 1/1991 | Morgan et al. | 424/1.1 |
| 4,994,553 | 2/1991 | Schmidt et al. | 530/327 |
| 5,002,869 | 3/1991 | Schlossman et al. | |

FOREIGN PATENT DOCUMENTS 8500522 2/1985 World Int. Prop. O. .............. 424/9

OTHER PUBLICATIONS

Arnaout, M. A. et al., "Inhibition of Phagocytosis of Complement C3-or Immunoglobulin G-Coated Particles and of C3bi Binding by Monoclonal Antibodies to a Monocyte-Granulocyte Membrane Glycoprotein (Mo1)," *J. Clin. Invest.* 72:171-179, 1983.

Haynes, B. F. et al., "Characterization of a Monoclonal Antibody (4F2) that Binds to Human Monocytes and to a Subset of Activated Lymphocytes," *J. Immunol.* 126:1409-1414, 1981.

Hofman, F. M. et al., "Heterogeneity of Macrophage Populations in Human Lymphoid Tissue and Peripheral Blood," *Cellular Immunology* 88: 61-74, 1984.

Lewandrowski, K. B. et al., "Expression of the Activation Antigen, 4F2, by Non-Hodgkin's Lymphomas of B-Cell Phenotype," *Cancer* 66:1158-1164, 1990.

Plum, J. et al., "Analysis of lymphocytes in tonsils and blood from patients with chronic tonsillitis," *Acta Oto-Rhino-Laryng., Belgica*, Tome 38, (Fasc. 6), 632-637, 1984.

Schulz, T. F. et al., "Antigenic relationship between the alpha-chain of C3, a leucocyte-surface antigen involved in the activation of phagocytic cells, and a 50,000 MW B-cell antigen," *Immunology* 54:791, 1985.

Wright, S. D. et al., "Identification of the C3bi receptor of human monocytes and macrophages by using monoclonal antibodies," *Proc. Natl. Acad. Sci. U.S.A.* 80:5699-5703, 1983.

*Primary Examiner*—C. Fred Rosenbaum
*Assistant Examiner*—Mark O. Polutta
*Attorney, Agent, or Firm*—Seed and Berry

[57] ABSTRACT

The present invention involves methods of enhancing the amount of target site localization of lymphoid cells. Methods of the present invention take advantage of the up-regulation of surface antigenic markers on lymphoid cells upon activation thereof. Imaging and therapeutic applications of such enhancement are described.

11 Claims, No Drawings

ENHANCEMENT OF TARGET CELL LOCALIZATION OF LYMPHOID CELLS

TECHNICAL FIELD OF THE INVENTION

The present invention involves therapeutic delivery and diagnostic targeting using lymphoid cells. Both passive administration and endogenous activation of lymphoid cells is contemplated by the present invention.

BACKGROUND ART

New interest has been awakened with respect to passive immunotherapy with activated lymphoid cells due to recent successes with LAK cells (lymphokine activated killer cells). For treatment, patients are administered IL-2 (interleukin-2) for priming and autologous cells are removed and activated ex vivo with IL-2. The activated cells, after a period of expansion, are then readministered to the patient along with IL-2 in order to maintain the lymphoid cells in an activated state. This form of therapy has been shown to be successful in both melanoma and renal cell cancer. In addition, numerous different schedules of IL-2 without LAK cells have been shown to enhance the production of endogenous circulating LAK cells. Other cell types, including PMNs and monocytes, can also be activated with a variety of lymphokines, including GM-CSF, G-CSF, gamma interferon, M-CSF, as well as TNF. With the discovery of colony-stimulating factors, the numbers of these cells can also be increased by enhancement of bone marrow progenitor survival. Thus, a variety of different cell types can be used for both passive as well as endogenous activated cell therapy.

However, a number of problems have been encountered which are typified by results with LAK cells. The first has to do with toxicity. Treatment with IL-2/LAK therapy or IL-2 alone has been shown to give rise to severe hypotension and edema. It has been recently demonstrated in vitro that nonspecificity of LAK cells may contribute to this toxicity. Second, studies with radiolabeled LAK cells, either derived from T or NK cells, have shown that these cells do not accumulate in tumors but primarily localize to RES (reticuloendothelial system) tissues. Thus, the mechanism of anti-tumor effect is not consistent with direct cytolytic action. Rather, these results are more consistent with effects caused by lymphokines secreted by the cells. Thus, in vitro studies which attempt to optimize direct cytolytic killing are probably not relevant to current clinical trials with LAK cells.

If one can increase tumor localization as well as reduce nonspecific binding to normal tissues, one can potentially improve therapy with these activated cells. Increased tumor localization will allow either direct cytolytic action or secretion of lymphokines in the region of the tumor as opposed to at a distance from the tumor. The specificity will assure that the direct cytolytic action is directed toward the appropriate target cells. Thus, enhanced localization and specificity of lymphoid cells is desired.

SUMMARY OF THE INVENTION

The present invention involves enhanced target site localization of lymphoid cells via passive administration of lymphoid cells activated ex vivo to a patient. Activated lymphoid cells are bound to an antibody capable of inhibiting the interaction of the lymphoid cells with other lymphoid cells and/or with the vascular endothelium to facilitate passage of such activated lymphoid cells through the vascular endothelium to the target site. The present invention also involves endogenous activation of lymphoid cells or lymphoid progenitor cells. Such activation is then followed by administration of a blocking antibody such as that described above to assist the lymphoid cells in accumulating at the target tissue site.

DETAILED DESCRIPTION OF THE INVENTION

The first aspect of the present invention involves a method of enhancing target site localization of lymphoid cells in a patient involving:
(1) withdrawing lymphoid cells from the patient;
(2) activating withdrawn lymphoid cells of step (1);
(3) combining activated lymphoid cells of step (2) with a blocking agent capable of blocking an adhesion receptor of the lymphoid cells; and
(4) infusing the combination of step (3) into the patient.

Lymphoid cells may be withdrawn from the patient via known techniques. For example, PMNs may be obtained by withdrawal of blood by venipuncture in heparinized tubes.

A common characteristic associated with activation of lymphoid cells regardless of their origin is the up-regulation of adhesion receptors. Such adhesion receptors, such as those termed LFA which are a part of the integrin family, are increased on PMNs (polymorphonuclear leukocytes), on monocytes, on LAK cells (lymphokine activated killer cells) or NK cells (natural killer cells) exposed to activation agents such as lymphokines.

More specifically, activation of leukocytes appears to take place in vivo as a result of an inflammatory response. Such activation may also be induced ex vivo for granulocytes by treatment with activators such as granulocyte-macrophage colony stimulating factor (GM-CSF), granulocyte colony stimulating factor (G-CSF), gamma interferon, a calcium ionophore or by other agents capable of inducing an oxidative burst. Similarly, monocytes can be activated with gamma-interferon, monocyte colony stimulating factor (M-CSF), colony stimulating factor-1 (CSF-1) or tumor necrosis factor (TNF). Natural killer (NK) cells can be activated with alpha and gamma-interferon and interleukin-2 and T-cells by interleukin-2, interleukin-4 and other interleukins.

Such activation may be accomplished via incubation of the withdrawn lymphoid cells with an appropriate activation agent, such as those described above, for a time sufficient to activate the lymphoid cells. This activation step may be done by known techniques.

Adhesion receptors normally function in regulation of homing of lymphoid cells to target sites. Target sites may be sites undergoing inflammation or an inflammation-like phenomena. Exemplary inflammatory target sites are sites of abscesses or bacterial infection. Target sites within the scope of the present invention also encompass tumor tissue sites.

This targeting process is regulated by LFA interactions with sequences on vascular endothelium, termed I-CAM. These interactions can regulate homing as well as govern entrance and exit of inflammatory cells into sites of inflammation. An increase in LFA expression upon activation of the lymphoid cells is a positive feature when such cells are already at the target sites because the cells are impeded from re-egress into the circulation, but is a negative feature when the cells are in the periphery and have to extravasate into or through tissues in order to get to the site of inflammation or tumor. By disrupting the interaction between adhesion proteins expressed by lymphoid cells and I-CAM, enhanced extravasation of lymphoid cells to target sites is achieved. Moreover, since receptors for chemotactic stimuli remain unblocked, the activated and blocked lymphoid cells can still chemotax efficiently.

Additionally, lymphoid cells express an I-CAM-like determinant as well. Sometimes designated as LEU-CAM, this marker promotes homotypic aggregation of lymphoid cells, such as PMNs and monocytes via LEU-CAM interaction with LFA. Disrupting this interaction will also disrupt LFA/I-CAM interaction.

Disruption of adhesion protein/I-CAM interaction (or adhesion protein/I-CAM-like moiety interaction) is accomplished by a blocking agent. A blocking agent may be any pharmaceutically acceptable moiety which binds to or associates with the adhesion protein or I-CAM in a manner sufficient to block the interaction between the two.

Exemplary of such blocking agents are antibodies or antibody fragments directed to LFA sequences which have been shown to be important in binding to I-CAM. Blockage of these LFA sequences will effectively block LFA/I-CAM interaction. Exemplary antibodies useful in the invention are directed to either the alpha or beta subunits of LFA or complement receptors 1 or 3. Antibodies useful in the invention have been described already in the literature and include antibodies such as OKM-1, MO-1, OKB-7 and 4F-2. Preferably, Fab or $F(ab')_2$ fragments of such antibodies are used in the practice of the present invention, since sensitization of the cells with a whole antibody will cause them to be removed rapidly through the RES system.

Other antibodies useful as blocking agents in the practice of this invention can be readily identified by known binding inhibition techniques with activated PMNs or monocytes or LAK cells with cells bearing I-CAM or I-CAM-like sequences. One example is LAK cells interacting with vascular endothelial cells. A second example is PMNs interacting with vascular endothelial cells. A third example would be PMNs or monocytic cell lines forming homotypic aggregates. PMNs, for example, also express a determinant designated as LEU-CAM, which is functionally similar to I-CAM in that it interacts with LFA determinants, thereby causing PMNs to aggregate. Antibodies which can inhibit these interactions are useful in the practice of this invention.

Peptides containing RGDS (arginine-glycine-aspartic acid-serine) sequences or other "I-CAM like" sequences, can also be used as the blocking agent in the process of the present invention. By "I-CAM like" sequences, there are contemplated sequences which are substantially functionally equivalent to I-CAM.

To illustrate, a blocking agent, such as an antibody fragment, is preincubated with LAK cells which have been generated by typical processes before reinfusion. Such blockage will allow the LAK cells to extravasate into tissues due to disruption of lymphoid cell interaction with I-CAM sequences on vascular endothelium. As the antibody fragment is lost from the lymphoid cell surface over time, these LAK cells will then be deposited in the tissue and not be able to re-enter the vascular system, because the LFA expressed by the lymphoid cells is now exposed and will interact with the vascular endothelium. Thus, the affinity of the fragment for its target antigen will govern the length of time which the cells can circulate and extravasate into tissues.

Binding of blocking antibody and withdrawn, activated lymphoid cells may be accomplished through incubation thereof. As can be readily seen from the foregoing, lymphoid cell activation may be accomplished prior to or concurrently with the incubation with the blocking antibody. The appropriate duration and conditions of this incubation step will depend on the lymphoid cell and antibody involved therein. A practitioner in the art would be able to determine appropriate incubation conditions.

In a modification of this aspect of the present invention, blocking agent can be infused separately upon reinjection of blocked, activated autologous lymphoid cells, to maintain the blockade of adhesion protein interaction with I-CAM and to ensure that lymphoid cells do not accumulate in the RES. This separate infusion is preferably concurrent with or closely subsequent to the infusion of blocked, activated lymphoid cells.

The infusion step may be conducted in any manner adequate to deliver the blocked, activated lymphoid cells and/or blocking agent to the bloodstream of the patient. Exemplary of acceptable administration routes are intraperitoneal, subcutaneous, intradermal, intraarterial or intravenous injection. The mode of administration is typically chosen according to the projected ultimate destination of the administered cells. Such infusions may be given as single or multiple injections. The blocked, activated lymphoid cells and/or blocking agent may be administered through injection directly into the vicinity of the target, where convenient.

In vivo administration of activated, blocked lymphoid cells and/or blocking agent may involve the use of pharmaceutical compositions in which the lymphoid cells are dispersed in a pharmaceutically acceptable carrier. Exemplary of such a pharmaceutically acceptable carrier is physiological saline or a physiologically acceptable buffer solution.

The lymphoid cells delivered to the target site will serve a therapeutic function via direct cytolytic action on target cells that are tumor cells, for example. Further, activated, autologous lymphoid cells may serve a therapeutic function via indirect cytolytic action in antibody-dependent, cell-mediated cytotoxicity (ADCC).

In addition, the blocked, activated lymphoid cells may also be covalently or non-covalently linked to a diagnostic agent, a therapeutic agent or both. This linkage is accomplished, for example, by associating a therapeutic or diagnostic moiety with the blocking agent, and incubating such a therapeutic or diagnostic agent - blocking agent conjugate with the activated lymphoid cells of the present invention. This incubation must be of a duration and under such conditions as to permit binding of the blocking conjugate to the lymphoid cells. A practitioner in the art would be able to determine suitable incubation conditions.

The radionuclide labeling of the present invention may be accomplished by covalently or noncovalently linking a moiety which generates an input for an imaging technique with the blocking agent. The label-blocking agent-lymphoid cell conjugate will be administered to the patient. Exemplary of labels useful in the present invention are radionuclides. This labeling may be done by conventional techniques. For example, Alvarez et al.

suggest methodologies for such labeling in U.S. Pat. No. 4,741,900.

Radionuclides are also useful as therapeutic agents for some disease conditions. Linking such radionuclides to the lymphoid cells of the present invention in the manner described above is also contemplated as a therapeutic embodiment thereof. Binding for either diagnostic or therapeutic purposes may be accomplished either prior or subsequent to the activation of the lymphoid cells and/or the incubation of such cells with blocking agent.

Radionuclides useful within the present invention include gamma-emitters, positron-emitters, Auger electron-emitters, X-ray emitters and fluorescence emitters, with beta- or alpha- emitters preferred for therapeutic use. Exemplary radionuclides are well-known in the art and include $^{111}$In, $^{51}$Cr, $^{188}$Re, $^{186}$Re, $^{198}$Au, $^{199}$Au, $^{113}$Ag, $^{111}$Ag, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101m}$Rh, $^{105}$Rh, $^{119}$Sb, $^{128}$Ba, $^{197}$Hg, $^{211}$At, $^{212}$Bi, $^{203}$Pb, $^{212}$Pb, $^{109}$Pd, $^{67}$Ga, $^{68}$Ga, $^{64}$Cu, $^{67}$Cu, $^{97}$Ru, $^{75}$Br, $^{76}$Br, $^{77}$Br, $^{99m}$Tc, $^{11}$C, $^{13}$N, $^{15}$O and $^{18}$F. Preferred therapeutic radionuclides include $^{188}$Re, $^{186}$Re, $^{203}$Pb, $^{212}$Pb, $^{212}$Bi, $^{109}$Pd, $^{64}$Cu, $^{67}$Cu, $^{90}$Y, $^{125}$I, $^{131}$I, $^{77}$Br, $^{211}$At, $^{97}$Ru, $^{105}$Rh, $^{198}$Au, and $^{199}$Au.

The present invention also contemplates radionuclide labeling of lymphoid cells via a chelating compound. Within this embodiment of the present invention, the conjugate to be administered to a patient may be described as follows:

radionuclide—chelate—blocking agent—lymphoid cell.

A chelating compound is a moiety capable of complexing with a radionuclide. Exemplary chelating compounds are those described in published European Patent Applications numbers 0188256, 0289187 and 0203764.

Other exemplary chelating compounds include compounds containing various combinations of nitrogen and sulfur atoms which act as the donor atoms for binding a metal or metal oxide. European Patent Application 0188256 discloses representative chelating compounds and their synthesis. A chelating compound within the present invention is a compound having four to six nitrogen and sulfur donor atoms. An example of a chelating compound contains two nitrogens and two sulfurs and is designated as "N$_2$S$_2$". Other chelating compounds useful in the practice of the present invention have different numbers of nitrogen and sulfur atoms. Examples of these chelating compounds are identified in like manner as "N$_3$S", "N$_2$S$_3$", "N$_2$S$_4$" and "N$_3$S$_3$". The following U.S. Patent Applications are hereby incorporated in their entirety by reference: U.S.S.N. 065,017 (filed June 19, 1987) "Metal Radionuclide Labeled Proteins For Diagnosis And Therapy"; U.S.S.N. 172,004 (filed March 23, 1988) "Metal-Radionuclide-Labeled Proteins And Glycoproteins For Diagnosis And Therapy"; U.S.S.N. 201,134 (filed May 31, 1988) "Metal Radionuclide Chelating Compounds For Improved Chelation Kinetics"; and U.S.S.N. 157,284 (filed Feb. 17, 1988) "Anchimeric Radiometal Chelating Compounds."

For example, the N$_2$S$_2$ metal chelating compounds may be dithio, diamino, diamidocarboxylic acids; amino/thio/amido combinations or derivatives thereof, e.g., a N,N'-bis-mercaptoacetyl, diamino carboxylic acid; esters capable of forming an amide bond in an aqueous medium; and intermediates of these esters.

Chelates useful in the present invention have a functional moiety capable of reacting with a blocking agent, thereby binding the chelate to that blocking agent. This chemically reactive group may be strongly electrophilic or nucleophilic, and thereby be available for reacting directly with a blocking agent. Alternatively, the moiety may be a weaker electrophile or nucleophile, and therefore require activation prior to binding with a blocking agent.

In either scenario, the chemically reactive moiety is, indeed, chemically reactive. The scenarios differ by whether the chemically reactive group is sufficiently reactive to be reacted directly with a blocking agent, or must first be activated first with one or more chemicals to render the group capable of reaction with a blocking agent. Illustrative chemically reactive groups and reactions thereof are described below.

Three methods are provided for producing the chelate-blocking conjugate useful in the method of the present invention. The first method features binding of the blocking agent to a radiolabeled compound, e.g., after a radiometal or radiometal oxide has been added to a chelating compound. A second method involves binding of the blocking agent to a fully formed, yet unlabeled, chelating compound, e.g., prior to the addition of a radiometal or radiometal oxide to the chelating compound. In both instances, the blocking agent is bound to the chelating compound via a chemically reactive group.

The step of combining a blocking agent with a labeled or unlabeled compound may be performed by direct reaction of the blocking agent with a chemically reactive moiety. This combination can also be achieved by "direct" reaction of a pre-activated chemically reactive moiety, as described above with a blocking agent. Alternatively, it may be desirable to include a preparatory step prior to the combining step to enhance the binding capability of the blocking agent. Such modification of the blocking agent may include reaction with any of the numerous bifunctional reagents reported in the literature.

A direct reaction involving a chelating compound and a modified or unmodified blocking agent requires a chemically reactive moiety capable of reacting with the modified or unmodified blocking agent. Exemplary chemically reactive moieties useful in the present invention include an alkyl group containing a good leaving group such as a halide, or a carbonyl-containing group such as an anhydride, an acid halide or an "active ester".

By an "active ester", there is contemplated esters that are highly reactive in nucleophilic substitution reactions. In the present invention, the modified or unmodified blocking agent would serve as the nucleophile. Typically, the esters will be activated phenols and cyclic compounds based upon hydroxylamine. Examples of commonly used "active" ester groups are tetrafluorophenyl, N-succinimidyl, nitrophenyl, isothiocyanate and substituted isothiocyanates. Alternatively, a chemically reactive moiety may serve as the nucleophile, such as an amino or sulfhydryl group capable of reacting with a modified blocking agent, e.g., a blocking agent containing a maleimide moiety.

Another preparatory step optionally used in the practice of the present invention is the activation of the chemically reactive moiety to enhance reactivity of the chelating compound with the blocking agent, as referred to above. Exemplary of such an activation is the conversion of a carboxyl moiety into an active ester. Another example is the activation of a chemical reactive moiety protected by a protective group. Removal of the protective group constitutes an activation. For example, removal of a phenylsulfonyl protective group from a succinimide derivative results in the conversion of the succinimide moiety into a maleimide moiety, which is highly reactive in nucleophilic addition reactions. Activation of the chemically reactive moiety also includes reaction of a nucleophilic moiety on the chelating compound with a bifunctional reagent. It will be evident to one skilled in the art that a variety of homobifunctional and heterobifunctional agents may be employed within the present invention to achieve such activation.

A third method for providing a radiolabeled blocking agent using a chelating compound bridge incorporates into the blocking agent a compound that is suitable for radiolabeling during the synthesis of such a compound. That is, a blocking agent is covalently attached to a precursor of a compound suitable for radiolabeling. Following this covalent attachment, the synthesis of the precursor compound is completed, such that the resultant chelating compound-blocking agent complex is suitable for radiolabeling.

In therapeutic applications of the present invention, drugs also may be attached to the blocking agent. Attachment of these therapeutic agents to the blocking agent may be accomplished by standard techniques. The choice of therapeutic agent will depend on the type of target cells involved. Attachment method and therapeutic agent choice are within the purview of practitioners in the arts of therapeutic design and treating physician. A list of exemplary pharmaceuticals for cancer therapy applications appears below.

Cancer chemotherapeutic agents such as nitrogen mustards, i.e., L-phenylalanine nitrogen mustard and cyclophosphamide; intercalating agents, such as cis diamino dichloro platinum; antimetabolites, such as 5-fluorouracil; porphrin and related compounds; vinca alkaloids, such as vincristine; and antibiotics, such as adriamycin and bleomycin. Other specific chemotherapeutic agents are daunorubicin, doxorubicin, methotrexate, aminopterin, vinblastine, vindesine, blenoxane, hematoporphyrin derivative, dihematoporphyrin ether, mitamycin, mithramycine and chlorambucil. These and other suitable chemotherapeutic agents are well-known in the art, and are in current clinical use and commercially available. Conventional chemotherapeutics are described in Cancer: *Principles and Practice of Oncology*, 2d ed., V. T. DeVita, Jr., S. Hellman, S. A. Rosenberg, J. B. Lippincott Co., Philadelphia, Pa, 1985, Chapter 14. Moreover, experimental drugs useful within the practice of the present invention are described in *NCI Investigational Drugs, Pharmaceutical Data* 1987, NIH Publication No. 88-2141, Revised November 1987.

Drugs known to enhance the cytotoxic effect of certain anti-cancer drugs and radiotherapeutic agents also may be used. Such drugs are commonly referred to as sensitizers. Exemplary sensitizers known to enhance the therapeutic effectiveness of radiation, for example, are metronidazole, misonidazole, certain 2-sulfamyl-6-nitrobenzoic acid derivatives, 2,6-disubstituted derivatives of 3-nitropyrazine and certain isoindoledione compounds. These and other suitable sensitizers are well-known in the art.

When the present invention is used for diagnostic purposes, imaging may be accomplished with the aid of one of the many commercially available imaging cameras, such as the Picker Digital Dynascan camera, the Raytheon LFOV Anger gamma camera and the gamma camera STARCAM made by General Electric Corporation. Visualization of sites of inflammation may be obtained by planar or single photon emission computed tomographic (SPECT) scans.

The time lapse between infusion of the labeled recognition agent and scan or imaging will vary somewhat with the patient's characteristics, i.e., body weight and condition, as well as the administration route, blocking agent and label used. Typically, a lapse of between 3 and 144 hours is required to allow the labeled blocking agent the opportunity to migrate to the target and clear from uninvolved tissue. An appropriate time lapse is readily determinable by a person ordinarily skilled in diagnostic imaging.

Images produced according to the present invention may aid in the detection of target sites. A diagnostician will recognize image patterns characterizing such an ailment. Also, the images produced according to the present invention will provide the diagnostician with information regarding the extent of the target site. Also, a sequence of images of an afflicted tissue site will permit monitoring of treatment protocols.

A second aspect of the present invention involves a method of enhancing target site localization of lymphoid cells in a patient including:

(1) inducing endogenous activation of lymphoid cells by infusing an activation agent into the patient; and
(2) infusing into the patient a blocking antibody capable of blocking an adhesion receptor of the lymphoid cells.

Activation may be induced in vivo by administering the appropriate activation agent or agents to the patient. Such activation may be induced for granulocytes by treatment with activators such as granulocyte-macrophage colony stimulating factor (GM-CSF), granulocyte colony stimulating factor (G-CSF), gamma interferon, a calcium ionophore or by other agents capable of inducing an oxidative burst. Similarly, monocytes can be activated with gamma-interferon, monocyte colony stimulating factor (M-CSF), colony stimulating factor-1 (CSF-1) or tumor necrosis factor (TNF). Natural killer (NK) cells can be activated with alpha and gamma-interferon and interleukin-2 and T-cells by interleukin-2, interleukin-4 and other interleukins.

The infusion step may be conducted in any manner adequate to deliver the activation agent to the bloodstream of the patient. Exemplary of acceptable administration routes are intraperitoneal, subcutaneous, intradermal, intraarterial or intravenous injection. The mode of administration is typically chosen according to the projected ultimate destination of the administered agent. Such infusions may be given as single or multiple injections.

In Vivo administration of activation agent may involve the use of pharmaceutical compositions in which the activation agent is dispersed in a pharmaceutically acceptable carrier. Exemplary of such pharmaceutically acceptable carrier is physiological saline or a physiologically acceptable buffer solution.

The time lag between steps (1) and (2) will be dependent on a variety of factors familiar to a diagnostician in a specific diagnostic and/or therapeutic field. Sufficient time must elapse to permit endogenous activation of lymphoid cells prior to the administration of the blocking agent.

Endogenous activation of lymphoid cells results in the up-regulation of lymphoid cell surface markers, such as the adhesion protein LFA. Subsequent infusion of blocking antibody will permit the activated lymphoid cells to extravasate into the target site more readily by blocking LFA/I-CAM interaction as described previously.

A third aspect of the present invention involves a method of enhancing target site localization of lymphoid cells in a patient including:
 (1) infusing a survival-enhancing agent into the patient to increase rate of survival of lymphoid progenitor cells thereby increasing the number of the lymphoid cells; and
 (2) inducing endogenous activation of lymphoid cells by infusing an activation agent into the patient; and
 (3) infusing into the patient a blocking antibody capable of blocking an adhesion receptor of the lymphoid cells.

Typically, only about half of the lymphoid progenitor cells mature into lymphoid cells. A survival enhancing agent is a moiety capable of increasing the survival rate of lymphoid progenitor cells. Increased progenitor survival results in increased mature lymphoid cell number. Exemplary survival enhancing agents are the colony stimulating factors for PMNs and monocytes.

The time lags between steps (1) and (2) and between steps (2) and (3) will be dependent on a variety of factors familiar to a diagnostician in a specific diagnostic and/or therapeutic field. Between steps (1) and (2), a time equivalent to or greater than the maturation time of lymphoid cells must pass. Between steps (2) and (3), a sufficient time must elapse to permit endogenous activation of lymphoid cells prior to the administration of the blocking agent.

A survival-enhancing agent increases the number of mature lymphoid cells. Endogenous activation of these lymphoid cells results in the up-regulation of lymphoid cell surface markers, such as the adhesion protein LFA. Subsequent infusion of blocking antibody will permit the activated lymphoid cells to extravasate into the target site more readily by blocking LFA/I-CAM interaction as described previously.

A fourth aspect of the present invention involves a method of enhancing target site localization of lymphoid cells in a patient including:
 (1) withdrawing lymphoid cells from the patient;
 (2) activating withdrawn lymphoid cells of step (1);
 (3) combining activated lymphoid cells of step (2) with a recognition agent capable of binding to an up-regulated surface antigen of lymphoid cells; and
 (4) infusing combination of step (3) into the patient.

As a recognition agent useful in the present invention, there is contemplated a monoclonal antibody or fragment thereof directed against a lymphoid cell activation marker. A lymphoid cell activation marker is a cell surface antigen which is poorly expressed or not expressed at all on lymphoid cells until the lymphoid cell is activated or caused to differentiate.

Preferably, the recognition agent is a monoclonal antibody or fragment thereof directed against an epitope of a lymphoid cell-associated antigen which is only expressed after activation, or which exhibits enhanced cell surface expression following activation. A useful activation marker within the present invention is one associated with a lymphoid cell surface antigen involved in chemotaxis, phagocytosis or cell killing which are functions normally enhanced with respect to activated lymphoid cells. Exemplary epitopes useful as activation markers include epitopes associated with the lymphocyte function associated antigens (LFA-1, LFA-2 and LFA-3), LEU-CAM, CD2, the LFA ligand, complement receptors CR1 and CR3, Fc receptors (I, II, III), a leukotriene receptor or a chemotactic factor receptor. Preferable chemotactic factor receptors recognize and bind C5a, C3a and formyl-methionine-leucine-phenylalanine (fMLP). Complement receptors include those for Clq and C3 fragments.

Recognition agents useful in the present invention selectively interact with activated lymphoid cells. That is, recognition agents of the present invention exhibit at least a 10-fold preference for binding to activated lymphoid cells over binding to non-activated lymphoid cells. For example, lymphoid cell receptor inhibitors are useful as recognition agents within the present invention.

The relationship between these antigens/epitopes and useful recognition agents may be further elucidated by way of example. As mentioned above, the C3 receptor is up-regulated upon lymphoid cell activation. As a result, monoclonal antibodies or fragments thereof specific for CR3 may be used as recognition agents. Normally, the expression of such receptor is below $10^3$ sites/cell and, therefore, insufficient for imaging. Up-regulation upon activation would both increase receptor number (making the receptor suitable for imaging) and increase receptor affinity (making it appropriate for imaging with labeled ligand). Thus, a ligand like a complement fragment may be labeled and used as a recognition agent in the practice of the present invention. Other exemplary ligands for up-regulated receptors include chemotactic peptides like fMLP, peptides derived from C3a and C5a capable of binding their respective receptors, immunoglobulin Fc peptides capable of binding Fc receptors, and complement components like Clq or C3 fragments capable of binding their respective receptors.

Recognition agents useful in the present invention may be linked to imaging inputs for use in diagnostic applications in the manner described above for blocking agents. Moreover, recognition agents may also be linked to therapeutic agents for use in therapy applications of the present invention in the manner described above for blocking agents.

An embodiment of the present invention features a monoclonal antibody or fragment thereof as a recognition agent directed against complement fragments that are bound at target sites or adsorbed to activated lymphoid cell receptors. A preferred embodiment of the present invention involves the use of a monoclonal antibody directed against C3dg. C3dg is an especially useful target for several reasons. First, C3dg is a cell- or tissue-bound activation product of the complement cascade, and will be present as a result of complement activation through the classical or alternative pathways. Second, since C3dg is the final degradation product of C3, antibodies directed to C3dg will assuredly react with tissue sites of activation, as opposed to antibodies directed to C3, C3b, or iC3b, which may react to determinants lost with further degradation. Third, antibodies to C3dg will be more sensitive in detecting target sites than antibodies to other complement components, since C3 activation represents the point of amplification in the complement cascade. For instance, for each molecule of Clq bound to cells or tissues, 100 molecules of C3b are bound. Fourth, antibodies to C3dg would have high selectivity for target sites similar to other antibodies to C3 fragments, since the presence of C3dg at any tissue site would require three different proteolytic cleavage steps, each regulated by a variety of mechanisms.

Eosinophilotactic peptides may also be used as recognition agents within the present invention. Exemplary peptides are VGDE (val-gly-asp-glu), VGSE (val-gly-ser-glu), VGAE (val-gly-ala-glu) and AGSE (ala-gly-ser-glu). These exemplary peptides are described in PNAS 72: 4123 (1975), *Immunology* 32: 57 (1977) and *Clinical Experimental Immunology* 43: 399 (1981). Eosinophilotactic peptides may be labeled through conventional techniques, preferably through the attachment of a spacer portion having a terminal tyrosine residue (the tyrosine residue may, of course, be attached after the spacer portion has been bound to the peptide). The tyrosine residue may then be radiolabeled.

As another recognition agent of the present invention, there is contemplated a chemotactic factor. A chemotactic factor is a factor that attracts polymorphonuclear lymphoid cells through a process called chemotaxis. Exemplary chemotactic factors useful in the present invention include chemotactic peptides such as fMLP and peptides of complement proteins, fragments thereof or derivatives or analogs thereof. Longer chemotactic peptides, such as fibrinopeptide B (pyroglu-G-V-N-D-N-E-E-G-F-F-S-A-R), may also be used in accordance with the present invention. Preferred complement proteins useful as recognition agents are C3a and C5a, fragments thereof or derivatives or analogs thereof. Exemplary analogs are: f-norLeu-L-P-norLeu-Y-K, wherein the tyrosine (Y) residue may be radiolabeled directly; and
f-norLeu-L-P-norLeu-;
boc-L-P-L-P-;
boc-M-L-P-
boc-P-L-F-L-F-;
boc-P-$L_D$-P-$L_D$-F-; and
f-M-L-Y-, wherein boc is T-butoxycarbonyl, $L_D$ is D-Leu and wherein the analogs may be labeled through conventional techniques, preferably through the attachment of a spacer portion having a terminal tyrosine residue (the tyrosine residue may, of course, be attached after the spacer portion has been bound to the peptide). The tyrosine residue may then be radiolabeled, if desired. These exemplary peptide analogs are described in *Science* 205: 1412 (1979), *Biochim. Biophys. Acta* 602: 85 (1980), *Nature* 272: 462 (1978), *PNAS* 73: 2439 (1976) and *Biochem. Biophys. Res. Comm.* 30: 464 (1978).

Also useful as recognition agents in the practice of the present invention are chemotactic peptide receptor inhibitors. Such inhibitors will bind to the chemotactic peptide receptor with high affinity. Peptides of complement protein C3a des Arg are also useful as recognition agents.

Chemotactic peptides may be prepared synthetically by conventional techniques. One embodiment of the recognition agent of the present invention involves the incorporation of D-amino acid(s) into a synthetic peptide chain, thereby decreasing in vivo degradation of the synthetic peptide. Degradative processes of the host recognize naturally-occurring L-amino acids. Thus, incorporation of one or more D-amino acids into the synthetic peptide enhances the stability of the peptide in vivo.

Another embodiment of the imaging method of the present invention as related to small synthetic peptides used as recognition agents involves the additional step of:

(5) comparing target site localization of the chemotactic peptide and reticuloendothelial system localization of the peptide, wherein exhibition of a substantial affinity of the peptide for circulating or reticuloendothelial cells necessitates step (6); and, if necessary, (6) altering the amino acid sequence of the peptide through addition or deletion of amino acids, so as to more closely correlate peptide structure with that bound by high affinity receptors of the activated lymphoid cells and less closely correlate with that bound by receptors of non-activated lymphoid cells, thereby producing a modified peptide capable of preferentially binding to activated lymphoid cells.

Peptide can be compared for binding to activated and non-activated cells. Modified or non-modified peptides are screened against activated and non-activated lymphoid cells for binding. A comparison of the difference in selectivity of peptides bound to activated and non-activated cells at different concentrations will indicate relative specificity of the peptide for activated and non-activated cells.

The comparison of step (5) may also be accomplished through analysis of an image obtained in the practice of the present invention. Such analysis is within the ordinary skill of a diagnostician familiar with diagnostic imaging of this type.

The alteration of step (6) may be accomplished by conventional protein synthetic techniques, following analysis of the binding to activated and non-activated cells. Activated lymphoid cells express receptors of higher affinity than non-activated lymphoid cells. Thus, recognition agents may be modified to more specifically associate with these high affinity receptors. Such alteration of recognition agents may be steric or chemical. That is, the change can serve to improve the steric "fit", i.e., the actual three-dimensional structural congruence of the peptide and the lymphoid cells, or to improve the chemical "fit", i.e., the correspondence of positively and negatively charged amino acids between the peptide and the lymphoid cell receptor.

Enhanced lymphoid cell recognition agent retention, may be obtained by substituting longer, more hydrophobic or charged amino acids to the chemotactic protein. These modified peptides may enhance the accumulation of label and/or therapeutic agent at target sites by increasing the peptide's ability to anchor to lymphoid cells, for example, by incorporation of a "spacer" amino acid portion to increase the length of the targeting peptide thereby increasing the accessibility of the peptide binding site to appropriate receptors on lymphoid cells.

Additional hydrophobic or like-charged polar "spacer" amino acid sequences can also be used to enhance peptide access to a receptor. For example, a chain of glycines (poly-G) could be added to the carboxy terminus of fMLP to increase chain length. A plurality of alanines (poly-A) may be added to produce a longer, more hydrophobic moiety. Aspartic acid (D) residues can be added to obtain a longer, negatively charged recognition agent while arginine (R) residues will impart positive charge as well as increased length. In each case, it may be necessary to include another amino acid, such as cysteine, to permit binding of the modified chemotactic peptide to a chelating compound.

Another procedure that may alter the serum half-life of the peptide (e.g., deliver an increased percentage of dose/gram to the target site) and increase affinity of the peptide for the target is conjugation of the peptide or peptide-spacer to a macromolecular carrier, such as albumin.

Monoclonal antibodies or fragments thereof of the present invention may be prepared according to conventional techniques. See, for example, Kohler and Milstein (1975, Nature 256: 495-97; 1976, Eur. J. Immunol. 6: 511-519).

Radiolabeling of antibodies and proteins may be accomplished through known techniques, such as those described in European Patent Application Publication Nos. 188256, 0289187 and 0203764. Alternatively, smaller, synthetically prepared peptides, such as fMLP, may be labeled by other techniques. For example, a synthetic peptide may be radiolabeled via tyrosine, lysine or cysteine or phenylalanine residue or analog thereof added to the peptide during conventional protein synthesis. Labeling such synthetic peptides may be done, for example, in two steps. First, the peptide having an additional residue is synthesized. Second, the residue is labeled by known techniques such as linking via a heterobifunctional chelate.

Recognition agents may also be linked to therapeutic agents in the practice of the present invention. Attachment of therapeutic agents to the recognition agent may be accomplished by standard techniques. The choice of therapeutic agent will depend on the type of target cells involved. Attachment method and therapeutic agent choice are within the purview of practitioners in the arts of therapeutic design and treating physician.

The method of this aspect of the present invention involves the additional step of combining activated lymphoid cells with a blocking agent as described previously either prior or subsequent to combining step (3). The conjugate administered in this embodiment of the present invention may be depicted as follows:

therapeutic agent or diagnostic agent
\
recognition agent ---lymphoid cell ---blocking agent.

Generally, the amount of the activated, blocked lymphoid cells, blocking agent, activating agent, survival-enhancing agent, recognition agent-lymphoid cell conjugate and recognition agent-blocking agent-lymphoid cell conjugate administered to a patient will depend primarily on the size of the patient and the purpose of the administration. However, the patient's physiological condition and the target site to be imaged or treated, if known, may impact the amount of agent necessary to obtain useful results. Practitioners in the specific diagnostic and therapeutic applications of the present invention will be able to determine appropriate dosage schedules.

For example, dosage of radionuclide label may readily be determined by one of ordinary skill in diagnostic imaging. A typical dose of radiolabel is between about 1 and about 3000 mCi. In humans, a standard imaging dose will be from about 1 to about 50 mCi, with about 10 to about 30 mCi being typical. Similarly, a standard therapeutic dose would be from about 50 to about 2000 mCi, with about 50 to about 700 mCi being typical.

To summarize the examples that follow, Example I describes the activation of polymorphonuclear leukocytes; Example II describes the activation of macrophage mononuclear leukocytes; Examples III, IV and V describe aggregation assays; Example VI describes aggregation and inhibition assays; Examples VII, VIII and IX describe inhibition assays; Examples X, XI, XII and XIII describe inhibition conjugates; Examples XIV and XV describe the preparation of chemotactic peptides useful in the present invention; Example XVI describes peptide-radiolabel conjugates; Examples XVII and XVIII describe monoclonal antibody generation (for use as a recognition agent within the present invention); and Examples XIX and XX describe monoclonal antibody (i.e., recognition agent) conjugates. These examples are offered as illustrations of the present invention and not as limitations thereof.

EXAMPLE I

Activation of Polymorphonuclear Leukocytes

Cytophoresis is performed on a patient, in order to obtain from peripheral blood a fraction enriched for mature PMNs. Briefly, the PMN enrichment technique involves standard blood phoresis performed in combination with hydroxyethyl starch, a sedimenting agent. The patient may also be pretreated with prednisone for 12 to 18 hours immediately preceding the phoresis process. Prednisone is a steroid that induces release of mature neutrophils from the bone marrow to the peripheral blood. The PMNs are collected under sterile conditions, with a typical cellular recovery approximating $30 \times 10^9$ cells/cytophoresis process.

The harvested PMNs are incubated for 15 to 30 minutes with 100 U/ml GM-CSF (recombinant human GM-CSF may be obtained from a COS cell transfectant (D. Metcalf et al., Blood 67:37-45, 1986)) in order to generate activated PMNs.

EXAMPLE II

Activation of Macrophages

Peripheral blood from a patient is obtained via venipuncture and fractionated by density centrifugation. That is, heparinized blood is layered onto Ficoll-Paque (Pharmacia), the gradient is centrifuged and the mononuclear cells are harvested from the plasma-gradient interface. The harvested cells are washed twice in serum-free RPMI 1640 medium. Monocytes are collected by adhering interface cells in RPMI 1640 containing 10% fetal calf serum and penicillin/streptomycin at $5 \times 10^6$ cells/milliliter. Adherent monocytes are incubated in the presence of a low pyrogen content M-CSF preparation (20 nanograms/milliliter, Genetics Institute) for 72 hours.

The following examples are indicative of the investigative protocol utilized in development of the present invention. First, the nature and extent of leukocyte autoaggregation (i.e., aggregation of leukocytes with other leukocytes) upon activation by various stimulators which up-regulate leukocyte activation antigens was examined. Second, monoclonal antibodies directed against up-regulated, activation antigens of leukocytes were made. This production step was conducted using established techniques. Third, generated monoclonal antibodies were screened against a variety of activation antigens to determine their ability to inhibit aggregation of leukocytes.

Examples III-V below set forth the results of aggregation assays done in conjunction with the first step of the investigative protocol described above. Example VI combines an aggregation assay of the first protocol step with an inhibition assay of the third protocol step referenced above. Examples VII-IX set forth below were done in conjunction with the third step of the investigative protocol.

EXAMPLE III

Aggregation Assay 90 cc of whole blood was extracted from a donor, and a 10 cc clot tube was employed to obtain an autologous serum sample from the donor. 5 cc serum was heat-inactivated at 56° C. for 30 minutes prior to use as autologous human serum within this example.

A 67 ml aliquot of whole blood was separated with fresh 3% dextran to obtain $255 \times 10^6$ PMNs ($3.8 \times 10^6$/ml blood) and $120 \times 10^6$ monocytes. PMNs and monocytes were purified over LSM (lymphocyte separation medium; Organon Teknika, Durham, N.C.), and the red blood cells were lysed with ACK (ammonium chloride/potassium carbonate buffer), as described in Arnaout et al., *J. Clin. Invest.* 7 78:599-601 (1986).

PMNs (50 microliters of $8 \times 10^6$/ml) were suspended in RPMI, and mixed with 50 microliters of either GM-CSF (100 U/ml final concentration), gamma interferon (400 U/ml final concentration), PMA (phorbol myristate acetate, 20 ng/ml final concentration) or RPMI (control). 100 microliters fetal calf serum (FCS) or autologous human serum (AHS) at 50%, 25%, 12%, 6%, 1% and 0.1% was added, and these mixtures were placed in duplicate 200 microliter wells and incubated at 37° C. (5% $CO_2$) for 2 hours.

Monocytes (50 microliters of $8 \times 10^6$/ml) were suspended in RPMI, and mixed with 50 microliter of either GM-CSF (10 U/ml final concentration), alpha interferon (500 U/ml final concentration), interleukin-2 (IL-2; 100 U/ml final concentration) or RPMI (control). Fetal calf serum (FCS) or autologous human serum (AHS) at 50%, 25%, 12%, 6%, 1% and 0.1% was added as above, and these mixtures were placed in duplicate 200 microliter wells and incubated at 37° C. (5% $CO_2$) for 2 hours.

Evaluation of the PMN controls indicated that high levels of FCS did not inhibit PMN autoaggregation, while no autoaggregation of PMNs was witnessed at 0.1% FCS. High levels of AHS appeared to be neutral toward or inhibitory of autoaggregation.

The presence of GM-CSF or gamma-interferon (especially in FCS-containing samples) promoted aggregation of PMNs. Granulocytes, as well as macrophages and certain T-suppressor cells, bear the Mo-1 determinant which appears responsible for GM-CSF-induced aggregation of cells (see Arnaout et al. referenced above).

In some experiments, PMNs were pre-incubated with GM-CSF. Removal of GM-CSF prior to incubation of PMNs with additional lymphokines had no effect on PMN aggregation.

Monocytes did not autoaggregate in the presence of lymphokines (GM-CSF, IL-2, gamma interferon) over a 2 hour incubation period. However, monocytes exhibited substantial aggregation upon incubation with IL-2 overnight.

EXAMPLE IV

PMN Aggregation Assay

7 PMNs were obtained from a donor, as described in Example III. PMNs (50 microliters of $4 \times 10^6$ cells/ml) were suspended in RPMI, and mixed with 50 microliters of either GM-CSF (10 U/ml final concentration), PMA (20 ng/ml final concentration), RPMI (control) or 100 microliters of GM-CSF plus IL-2 (10 U/ml and 100 U/ml final concentration, respectively). FCS and non-autologous serum was added and the mixture was assayed as in Example III.

GM-CSF stimulated aggregation of PMNs when administered alone or in conjunction with IL-2. Thus, IL-2 did not inhibit the GM-CSF stimulation of PMN aggregation.

Non-autologous human serum had an inhibitory effect on aggregation of PMNs at high serum concentrations, as noted for autologous human serum in Example III. The effect of human serum on PMN aggregation was variable and donor dependent.

EXAMPLE V

Aggregation of Monocytes Activated in Presence of PMNs

Cells were set up in 12 well cluster dishes at 5 ml/well overnight. The number of monocytes (MN; $12.5 \times 10^6$ per culture) was limiting. The cultures prepared were as follows:

| Cells | Serum | Lymphokines | Additional |
|---|---|---|---|
| MN only | 5% FCS | none (control) | none |
| | | GM-CSF (10 U/ml) | |
| | | IL-2 (100 U/ml) | |
| | | GM-CSF + IL-2 | |
| MN + PMN 1:1 | 5% FCS | none (control) | none |
| | | GM-CSF (10 U/ml) | |
| | | IL-2 (100 U/ml) | |
| | | GM-CSF + IL-2 | |
| | | GM-CSF + IL-2 | *anti-gamma-INF |
| | | GM-CSF + IL-2 | OKM-1 |
| | | GM-CSF + IL-2 | |
| | | IL-2 | |

*Anti-gamma-interferon (INF) was added to a final neutralizing equivalent of 400 U/ml (i.e., capable of neutralizing 400 U/ml gamma-interferon). OKM-1 added was at a final concentration of 10 micrograms/ml. Indicated concentrations of lymphokines are final concentrations.

Aggregation within the cultures was determined at 2 hours or 24 hours. AHS did not produce "nonspecific" aggregation (i.e., aggregation in the absence of an activator), such as observed with FCS at both concentrations tested.

EXAMPLE VI

PMN and LAK Aggregation and Inhibition Assays

Monocytes were incubated for 4 days in RPMI +1% FCS +IL-2 (100 U/ml). $12 \times 10^6$ day 4 LAK cells were harvested, and $1 \times 10^5$ LAK cells in RPMI +1% FCS were then incubated with 50 microliters RPMI (control), OKM-1 monoclonal antibody microgram/well) or PMA (20 nanograms/ml). The aggregation assay was performed as above, using either FCS, autologous human serum or AB-negative human serum. OKM-1 monoclonal antibody binds an epitope of the CD11b cluster, designated variously as MO-1 and MAC-1 (see Arnaout et al., J. Clin. Invest. 78:599-601 (1986)). This epitope is known to be up-regulated on PMNs by GM-CSF and involved in cell-cell adhesion (aggregation).

$1 \times 10^5$ PMNs in RPMI were incubated with 50 microliters RPMI (control), GM-CSF alone (10 U/ml) or GM-CSF (10 U/ml) plus OKM-1 monoclonal antibody (1 microgram/well). The aggregation assay was performed as above, using either FCS, autologous human serum or AB-negative human serum.

For PMNS, aggregation was enhanced by the presence of GM-CSF. For LAK cells, considerable autoaggregation was observed in the control samples. Intact OKM-1 appeared to cross-link cells, rather than inhibit aggregation.

EXAMPLE VII

Inhibition of Aggregation of LAK Cells $4 \times 10^5$ day 3 LAK cells were combined with 5, 1, 0.2, 0.04, 0.008, or 0.0016 micrograms/well of either anti-CR-I (Becton-Dickinson Immunology, Mountain View, CA), anti-C3biR (Dako Corp., Santa Barbara, CA), anti-CD11b (AMAC, Inc., Westbrook, ME), 4F-2 (an anti-human monocyte antibody secreted by the hybridoma cell line designated "4F2C13", ATCC, Rockville, MD), anti-LFA-1 (AMAC) or OKM-1 (Ortho Diagnostic Systems, Raritan, N.J.) antibody in 1% FCS. The LAK cells and antibody preparations were placed in duplicate 200 microliter wells and incubated at 37° C. (5% $CO_2$) for 2 hours.

Day 3 LAK cells exhibited less aggregation than the day 4 LAK cells tested in Example VI. The highest level of aggregation inhibition observed was at an antibody concentration of 0.0016 micrograms/well. This antibody concentration corresponded to approximately $1.5 \times 10^4$ IgG/LAK cell. Because inhibition could be achieved at this low concentration of whole antibody, aggregation inhibition should be attainable using fragments of whole antibody, such as Fab.

EXAMPLE VIII

Aggregation Inhibition of PMNs With Pre-Incubation

PMNs were obtained from a donor as described previously, and purified PMNs were suspended in RPMI to a concentration of $8 \times 10^6$/ml. Pre-incubation of PMNs was conducted in bulk by mixing $64 \times 10^6$ cells/8 ml with 10 U/ml GM-CSF for 15 minutes.

$4 \times 10^5$ of pre-incubated PMNs were combined with 1, 0.2, 0.04, 0.008, 0.0016 and 0.00032 micrograms/well of either anti-CR-I (Becton-Dickinson; B-D), anti-CR-III (B-D), anti-C3biR (Dako), anti-CDllb (AMAC), 4F-2, anti-iC3b (Cytotech, San Diego, Calif.), anti-LFA-1 (AMAC) or OKM-1 (Ortho) antibody in 5% FCS. 50 microliters of RPMI was used as the control in this experiment. These mixtures were assayed in the manner described in Example VII.

A marked increase in aggregation of PMNs was observed upon pre-incubation of PMNs with GM-CSF. No marked aggregation inhibitory effects were observed with any of the intact antibodies tested. Because the Fab portion of the antibody binds to adhesion markers of PMNs, while the Fc portion of the antibody serves to cross-link two PMNs by binding to Fc-gamma-R of other PMNs, Fab fragments are preferred for testing aggregation inhibition.

EXAMPLE IX

PMN Aggregation Inhibition

PMNs were extracted from a donor, as described in Example III. $4 \times 10^5$ PMNs alone, PMNs plus 10 U/ml GM-CSF (simultaneous), or PMNs pre-incubated with GM-CSF for 15 minutes were combined with 0.25, 0.12, 0.06, 0.03, 0.015 and 0.008 micrograms/well of either anti-CR-I (B-D), 4F-2, anti-LFA-1 (AMAC), anti-Tac (T. Waldmann, NCI, Bethesda, MD), leu-M3 (B-D) or OKM-1 (Ortho) antibody in a serum diluent. PMNs were pre-incubated in accordance with Example VIII.

The serum diluent for these assays was either 1% FCS or 50% heat-inactivated AHS or 0.1% mouse albumin (Boehringer-Mannheim Biochemicals, Indianapolis, Ind.). The mixtures were assayed as in Example VII.

A significant decrease in aggregation (true and false positives) was seen in the mouse albumin assay samples, especially with OKM-1 and anti-LFA-1, indicating antibody inhibition of aggregation. Mouse albumin, itself, did not inhibit aggregation. In the "PMN alone" samples, mouse albumin appeared to enhance aggregation.

EXAMPLE X

Activated Autologous PMN/Labeled I-CAM Interaction Inhibitor Conjugate

Fab fragments of 4F-2 (an anti-human monocyte antibody produced by the hybridoma cell line designated "4F2C13", ATCC, Rockville, Md.) capable of blocking LFA/I-CAM interaction are radiolabeled in accordance with the procedure described in European Patent Application Publication No. 0188256. Activated PMNs prepared in accordance with Example I are incubated with these radiolabeled antibody fragments for 60 minutes. Conjugates formed from this incubation are then infused into a patient.

EXAMPLE XI

LAK Cell - Antibody Conjugate

LAK cells preincubated for 4 days with IL-2 are admixed with Fab of OKM-1 antibody (Ortho) and incubated therewith for 2 hours. The conjugate thereby formed is then administered to a patient.

Administration of such a conjugate will allow the LAK cells to extravasate into tissues, due to blocking of interaction with I-CAM sequences on vascular endothelium. As the Fab is lost from the cell surface, these LAK cells will then be deposited in tissues and not be able to extravasate into the vascular system. Thus, the affinity of the Fab for its target antigen will govern the length of time that the cells can circulate and extravasate into tissues.

EXAMPLE XII

LAK Cell Conjugation/LAK Cell Endogenous Activation

LAK cells preincubated for 3 days with IL-2 are admixed with Fab of OKM-1 antibody (Ortho) and incubated therewith for 2 hours. The conjugate thereby formed is then administered to a patient.

Alternatively, activated LAK cells are created endogenously by administering IL-2 and then Fab of OKM-1. In this scenario, the Fab fragment is administered to coat the LAK cells, thereby allowing their extravasation into tissue.

EXAMPLE XIII

PMN - Antibody Fragment Conjugates

PMNs are activated with GM-CSF and are then preincubated with an $F(ab')_2$ fragment of antibody OKM-1 for 60 minutes. The PMN-antibody conjugates thus formed are administered to a patient. Conjugation of antibody fragments and leukocytes serves to block the ability of the PMNs to interact with vascular endothelium, thus allowing them to extravasate better into sites of inflammation around tumors or regions of replication of infectious organisms (abscesses). This results in improved imaging if the cells are labeled, or improved killing of bacteria or tumor targets.

EXAMPLE XIV

Preparation of Stabilized, Labeled Chemotactic Peptide

The chemotactic peptide met-leu-phe, having an additional Gly-Gly-Lys moiety, is synthesized using teabag methodology and solid phase peptide synthesis procedures described by Merrifield et al. (*Biochemistry* 21: 5020-31, 1982) and Houghten (*Proc. Natl. Acad. Sci. (USA)* 82: 5131-35, 1985), using a commercially available automated synthesizer, such as the Applied Biosystems 430 A or using other standard biochemistry techniques. The peptide is cleaved from the resin using HF and established procedures and extracted with dilute acetic acid. The peptide is lyophilized and is purified using reverse phase HPLC on a Vydac C-4 analytical column (The Separations Group, Hesperia, CA), and a linear gradient of 0.5-1.0%/min from 100% water +0.1% v/v trifluoroacetic acid to 100% acetonitrile +0.1% trifluoroacetic acid. The peptide is N-formylated via reaction with acetic anhydride in 98% formic acid for 1 hour at 25° C., as described in *J. Am. Chem. Soc.* 80: 1154 (1958). Iodine labeling of the lysine residue is accomplished as described by Panuska and Parker (*Analytical Biochemistry* 160: 192-201, 1987).

EXAMPLE XV

Preparation of Chemotactic Peptide Derivatives

The chemotactic peptide analog boc-L-F-L-F having a chain of amino acids, such as -G-G-G-G-G-Y, at its amino terminus is synthesized as described in *Biochim. Biophys. Acta* 602: 285 (1980) or using a commercially available automated synthesizer, such as the Applied Biosystems 430 A or using other standard biochemistry techniques. The peptide is lyophilized and is purified using reverse phase HPLC on a Vydac C-4 analytical column (The Separations Group, Hesperia, CA), and a linear gradient of 0.5-1.0%/minute from 100% water +0.1% v/v trifluoroacetic acid to 100% acetonitrile +0.1% trifluoroacetic acid. Iodine labeling of the peptide is accomplished as described in European Patent Application publication No. 0289187. The longer chemotactic peptide derivative enhances target cell label retention.

EXAMPLE XVI

Peptide-Radiolabel Conjugations

A Tc-99m chelate is conjugated to the unlabeled chemotactic peptide of Examples XIV or XV as follows. 75 mCi of Tc-99m chelated by N, N'-bismercaptoacetyl 4,5-diaminopentanoic acid is prepared by dithionite reduction of Tc-99m pertechnetate at basic pH with 25 micrograms of the $N_2S_2$ ligand. The acid is activated by adding the above complex at pH 7 in 0.5 ml water to 100 microliters of water:acetonitrile (1:9) containing 3.0 milligrams of 2,3,5,6-tetrafluorophenol and 100 microliters of water:acetonitrile (1:9) containing 7.5 milligrams of 1-cyclohexyl-3-(2-morpholinoethyl)carbodiimide (morpho CDI). After storing for 18 hours at room temperature, the mixture is purified using a Baker-10 SPE reversed phase $C_{18}$ a column. The column is conditioned with 2 milliliters of ethanol and is then washed with HPLC grade water. The reaction mixture is then added to the column, the column is then washed four times with 2 milliliter volumes of 10% methanol in 0.01 sodium phosphate, pH 7.0 and the ester complex is finally eluted with 2.5 milliliter portions of acetonitrile.

To a 2 milliliter vial is added 4.5 mCi of activated ester complex in acetonitrile, the solvent is evaporated in a nitrogen stream, and 0.4 milliliters of sodium borate (0.5M, pH 9.0) is added. While agitating, the chemotactic peptide is added and incubation at room temperature is conducted for 30 minutes.

EXAMPLE XVII

Monoclonal Antibody Generation

Mice are immunized with homotypic aggregates of activated PMNs pooled from normal donors. This pooling of PMNs is accomplished through the withdrawal of blood (in amounts of approximately 150 cc) by venipuncture in heparinized tubes and mixing with an equal volume of 3% dextran in phosphate-buffered saline (PBS). After sedimentation at 1×g for 10 minutes at room temperature, the leukocyte-rich plasma is layered on top of lymphocyte separation medium (LSM, Organon Technica, Durham, N.C.). PMNs are purified by treating the PMNs and the red blood cell (RBC) pellet with RBC lysing solution (0.800% w/v $NH_4Cl$, 0.1% w/v $KHCO_3$, 37.0 mg tetrasodium EDTA in 100 ml water at pH 7.3). After incubating approximately 5 minutes at room temperature, the volume is increased three times with PBS and the cells are washed twice by centrifugation. The PMNs are incubated for 15 to 30 minutes with 100 U/ml GM-CSF in the presence of human serum to generate activated PMNs which are capable of forming homotypic aggregates.

These aggregated PMNs are then injected into mice as an immunogen. Hybridomas generated by the immunogen are then screened against activated or nonactivated pooled PMNs in the presence of human serum. Desirable antibodies are those that recognize activation markers as well as conformation-dependent determinants (in this case, PMN-PMN aggregates). The antibodies identified as desirable are further screened against inflammatory lesions using immunoperoxidase techniques.

EXAMPLE XVIII

Monoclonal Antibody Generation

Mice are immunized with heterotypic aggregates prepared in vitro and having activated PMNs pooled from normal donors as one component of the heterotypic aggregate. This pooling of PMNs is accomplished through the withdrawal of blood (in amounts of approximately 150 cc) by venipuncture in heparinized tubes and mixing with an equal volume of 3% dextran in phosphate-buffered saline (PBS). After sedimentation at 1×g for 10 minutes at room temperature, the leukocyte-rich plasma is layered on top of lymphocyte separation medium (LSM, Organon Technica, Durham, N.C.). PMNs are purified by treating the PMNs the and red blood cell (RBC) pellet with RBC lysing solution (0.800% w/v $NH_4Cl$, 0.1% w/v $KHCO_3$, 37.0 mg tetrasodium EDTA in 100 ml water at pH 7.3). After incubating approximately 5 minutes at room temperature, the volume is increased three times with PBS and the cells are washed twice by centrifugation.

The activated PMNs are incubated with either vascular endothelial cells or portions thereof, bacteria or other pathogenic organisms or target tissue (tissue afflicted with inflammation). This incubation is conducted for a time sufficient (approximately 30 minutes) to permit association of the activated PMNs with the vascular endothelial cells, the commencement of phagocytosis with respect to the pathogenic organisms, or attachment of the activated PMNs and the target cells.

One type of heterotypic aggregate is then injected into mice as an immunogen. Hybridomas generated by the immunogen are then screened against activated or non-activated pooled PMNs in the presence of human serum. Desirable antibodies are those that recognize activation markers as well as conformation-dependent determinants (in this case, epitopes present on PMN-vascular endothelium aggregates, PMNs undergoing phagocytosis or PMN-target cell aggregates). The antibodies identified as desirable are further screened against inflammatory lesions using immunoperoxidase techniques.

EXAMPLE XIX

Antibody-Radiolabel Conjugation

In an evacuated vial is combined 100 microliters of water, 100 microliters acetonitrile, 100 microliters of citrate solution (28.8 milligrams, $1.5 \times 10^{-4}$ mol), 50 microliters of ligand (tetrafluorophenyl 4,5-di(tetrahydropyranylmercapto-acetamido)pentanoate; 0.40 milligrams; $6.5 \times 10^{-7}$ mol), 50 microliters of stannous chloride (0.5 milligrams, $2.6 \times 10^{-6}$ mol), and 50 microliters of Tc-99m in acetonitrile (4.25 micrograms, $2.3 \times 10^{-8}$ mol) The mixture is heated at 50° C. for one hour and then 0.30 milliliters of 1N NaOH is added.

The tetrafluorophenyl ester product of the Tc-99m $N_2S_2$ complex is purified on a $C_{18}$ a Baker-10 SPE column. After application to the column, impurities are washed off with $2 \times 3$ milliliters of water and $4 \times 3$ milliliters of 10% $CH_3OH/0.01M$ phosphate, pH 7. The product is eluted with 2 milliliters of acetonitrile and then the solution is reduced to dryness under a stream of nitrogen.

Conjugation of the Tc-99m $N_2S_2$ complex is done by addition of the antibody of Example XVII or Example XVIII to the complex in borate buffer (0.5M, pH 9). Incubation is maintained for 30 minutes at room temperature.

EXAMPLE XX

Antibody-Radiolabel Conjugations

A Tc-99m chelate is conjugated to the monoclonal antibody of Example XVII or Example XVIII as follows. 75 mCi of Tc-99m chelated by N, N'-bismercaptoacetyl 4,5-diaminopentanoic acid is prepared by dithionite reduction of Tc-99m pertechnetate at basic pH with 25 micrograms of the $N_2S_2$ ligand. The acid is activated by adding the above complex at pH 7 in 0.5 ml water to 100 microliters of water:acetonitrile (1:9) containing 3.0 milligrams of 2,3,5,6-tetrafluorophenol and 100 microliters of water:acetonitrile (1:9) containing 7.5 milligrams of 1-cyclohexyl-3-(2-morpholinoethyl)carbodiimide (morpho CDI). After storing for 18 hours at room temperature, the mixture is purified using a Baker-10 SPE reversed phase $C_{18}$ column. The column is conditioned with 2 milliliters of ethanol and is then washed with HPLC grade water. The reaction mixture is then added to the column, the column is then washed four times with 2 milliliter volumes of 10% methanol in 0.01 sodium phosphate, pH 7.0 and the ester complex is finally eluted with 2.5 milliliter portions of acetonitrile.

To a 2 milliliter vial is added 4.5 mCi of activated ester complex in acetonitrile, the solvent is evaporated in a nitrogen stream, and 0.4 milliliters of sodium borate (0.5 M, pH 9.0) is added. While agitating, the antibody is added and incubation at room temperature is conducted for 30 minutes.

What is claimed is:

1. A method of enhancing target site localization of lymphoid cells in a patient comprising:
    (1) inducing endogenous activation of lymphoid cells by infusing an activation agent into said patient; and
    (2) infusing into said patient a blocking agent which blocks an adhesion receptor of said lymphoid cells.
2. A method of claim 1, wherein said lymphoid cells are selected from the group consisting of T cells, polymorphonuclear leukocytes and monocytes.
3. A method of claim 1, wherein said activation agent is granulocyte-macrophage colony stimulating factor, granulocyte colony stimulating factor, tumor necrosis factor or gamma-interferon and said lymphoid cells are polymorphonuclear leukocytes.
4. A method of claim 1, wherein said activation agent is gamma-interferon, granulocyte-macrophage colony stimulating factor, monocyte colony stimulating factor or tumor necrosis factor and said lymphoid cells are monocytes.
5. A method of claim 1, wherein said activation agent is interleukin-2 and said lymphoid cells are T cells or natural killer cells.
6. A method of claim 1, wherein said adhesion receptor is a lymphocyte function associated antigen.
7. A method of claim 1, wherein said blocking agent is a monoclonal antibody or a fragment thereof.
8. A method of claim 7, wherein said fragment is Fab.
9. A method of claim 7, wherein said fragment is F(ab')$_2$.
10. A method of claim 7, wherein said monoclonal antibody or fragment thereof is selected from the group consisting of OKM-1, MO-1, OKB-7 and 4F-2.
11. A method of claim 1, wherein said blocking agent is covalently or non-covalently linked to a diagnostic agent, a therapeutic agent or both.

* * * * *